United States Patent
Saxena et al.

(10) Patent No.: US 10,507,184 B2
(45) Date of Patent: Dec. 17, 2019

(54) IMPLANTABLE NALTREXONE TABLETS

(71) Applicant: RUSAN PHARMA LIMITED, Mumbai (IN)

(72) Inventors: Navin Saxena, Mumbai (IN); Kunal Saxena, Mumbai (IN)

(73) Assignee: RUSAN PHARMA LIMITED, Kandivali (West) Mumbai (IN)

(*) Notice: Subject to any disclaimer, the term of this patent is extended or adjusted under 35 U.S.C. 154(b) by 0 days.

(21) Appl. No.: 15/755,374

(22) PCT Filed: Aug. 23, 2016

(86) PCT No.: PCT/IN2016/050280
§ 371 (c)(1),
(2) Date: May 2, 2018

(87) PCT Pub. No.: WO2017/033208
PCT Pub. Date: Mar. 2, 2017

(65) Prior Publication Data
US 2018/0338925 A1    Nov. 29, 2018

(30) Foreign Application Priority Data
Aug. 24, 2015 (IN) .................. 3223/MUM/2015

(51) Int. Cl.
*A61K 9/20* (2006.01)
*A61P 25/00* (2006.01)
*A61K 31/485* (2006.01)
*A61P 3/04* (2006.01)
*A61K 9/00* (2006.01)

(52) U.S. Cl.
CPC .......... *A61K 9/2027* (2013.01); *A61K 9/0024* (2013.01); *A61K 9/204* (2013.01); *A61K 9/2013* (2013.01); *A61K 31/485* (2013.01); *A61P 3/04* (2018.01); *A61P 25/00* (2018.01)

(58) Field of Classification Search
None
See application file for complete search history.

(56) References Cited

U.S. PATENT DOCUMENTS

| | | | | |
|---|---|---|---|---|
| 4,874,612 A | * | 10/1989 | Deasy | A61K 9/0024 424/425 |
| 7,914,804 B2 | * | 3/2011 | O'Neil | A61K 9/0024 424/422 |
| 2004/0254208 A1 | * | 12/2004 | Weber | A61K 31/135 541/282 |

(Continued)

FOREIGN PATENT DOCUMENTS

| CN | 102512399 A | * | 6/2012 |
| RU | 2476209 C1 | * | 2/2013 |

OTHER PUBLICATIONS

Machine translation of CN-102512399-A, 2012. (Year: 2012).*
Machine translation of RU-2476209-C1, 2013. (Year: 2013).*

*Primary Examiner* — Carlos A Azpuru
*Assistant Examiner* — Casey S Hagopian
(74) *Attorney, Agent, or Firm* — Kramer Amado, P.C.

(57) ABSTRACT

The invention discloses naltrexone implantable tablets which are devoid of metal salts and corticosteroids, and which provide consistent and controlled amount of naltrexone for 3 months or more; also disclosed is methods of treatment comprising the implants and methods of sterilization of the implants.

15 Claims, 1 Drawing Sheet

(56) References Cited

U.S. PATENT DOCUMENTS

2009/0208540 A1\* 8/2009 Kuzma ................ A61K 9/0024
424/400
2013/0084333 A1\* 4/2013 Dick .................... A61K 9/2095
424/465

\* cited by examiner

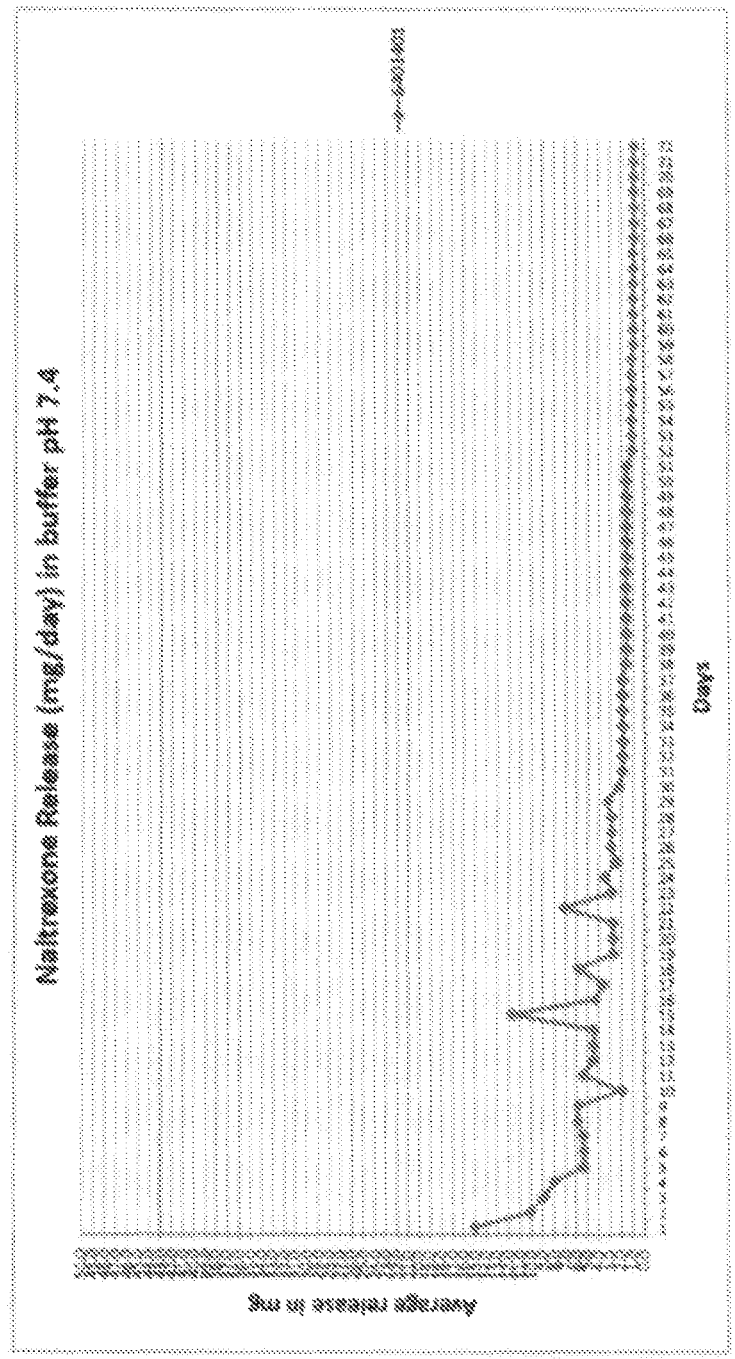

IMPLANTABLE NALTREXONE TABLETS

FIELD OF INVENTION

This invention relates to implantable tablets of an opioid antagonist, or a salt thereof. In certain embodiments, provided herein are naltrexone implantable tablets which provide consistent and controlled amount of Naltrexone for 3 to 6 months. Also disclosed is a process for preparation and sterilization of naltrexone implantable tablets.

Background and Prior Art

Drug and alcohol abuse are often symptomatic of underlying social issues, and can be coupled with unregulated behavior such as unsafe sexual practices and HIV/AIDS risk, all of which are evidenced in the currently prosperous states. The enormity of the problem is not known to any degree of accuracy, but all available evidence is indicative of a disaster in the time to come, and requires urgent attention from all stakeholders. A sizeable population of world, and particularly of young people, highlights the need for multi-layered interventions to avert disaster in the economically productive generations of today and tomorrow.

Naltrexone is an opioid receptor antagonist used primarily in the management of alcohol and opioid dependence. It is marketed in the generic form as its hydrochloride salt, naltrexone hydrochloride. It is marketed under the trade names Revia and Depade in the form of 50 mg film coated tablets.

However, these oral tablets only have duration of action of around 24 to 48 hours and has been reported that most patients who are heavily dependent on opioid either forget or purposefully choose not to take their medicine and the treatment become ineffective to overcome the dependence. To circumvent the above problem once monthly depot injections have been developed that do not allow the patient to forget or skip their medicine, which releases a controlled amount of naltrexone into the body, to make the treatment effective. In many countries including in US, a once monthly extended release injectable formulation (depot injection) is marketed under the trade name Vivitrol. Naltrexone has also been shown to decrease heroin and amphetamine use. Recently, naltrexone implants are in the market for the treatment of variety of addictions including to drugs and alcohol. A naltrexone implant is a small pellet that is inserted into the body, for example into the lower abdominal wall under local anesthetic. Such an implant is typically effective for 3-6 months depending on the type of implant used, and releases a controlled amount of naltrexone into the body. The implant works by blocking the effects of opiate drugs. However, current naltrexone implants have side effects including infection, irritation, and inflammation at the site of implantation.

Naltrexone therapy is often given for a minimum of 6 to 12 months in order to give the patient time to recover from addiction, to lead normal life post recovery, and in certain cases, to recover from the brain damage from the narcotics.

Naltrexone implantable tablets were first reported in WO1998030171 by Lance L Gooberman. In these tablets, naltrexone is embedded in magnesium stearate complex. These implants are reported to cause tissue irritation due to magnesium stearate. These implants are reportedly claimed to dissolve and disappear completely in about 5-6 weeks on average. This requires frequent repeat of the implant procedure, which raises the risk of infection and other surgical complications.

A different type of naltrexone 1000 mg implant has been developed by George Sherman at Towne Pharmacy, NJ by combining with slow-release 100 mg triamcinolone, a corticosteroid, to reduce tissue reactions. This type of implant reportedly gives effective opioid blockage for 12 to 14 weeks. These implants are currently marketed in Russia under trade name "Prodetoxone pellets". However, triamcinolone is known to cause side effects such as sore throat, nosebleeds, increased coughing, headache, and runny nose and can cause allergic reactions with symptoms including rash, itch, swelling, severe dizziness, and trouble breathing. Furthermore, in the naltrexone implant context, triamcinolone introduced into the composition to resolve irritation and inflammation has been found to contribute unwanted side effects: as disclosed herein, introduction of corticosteroids such as triamcinolone acetonide even in small amounts (e.g., 30 mg) into the body of a mammal via implantable tablets, appears to cause significant loss of body weight accompanied by lethargy. Other corticosteroids (e.g., prednisolone and hydrocortisones) can have equally serious side effects if used in naltrexone implants to reduce/control inflammation/irritation at the site of implantation caused by the presence of magnesium salts in the composition. Corticosteroid side effects tend to increase with duration of treatment, making long-term corticosteroid treatment inadvisable. And in any case, multiple pharmaceutical actives in a single dose increases metabolic load on the liver.

Yet another version of implants of naltrexone has been developed by Dr George O'Neill of GO-Medical Industries which comprises naltrexone embedded in a matrix of biodegradable polymer microspheres. These implants have been reported to release naltrexone for 5-12 months or more. The composition of the O'Neill implant comprises approximately 50% naltrexone, 49% of biodegradable polymer and less than 1% magnesium stearate. These implants are normally inserted under antibiotic prophylaxis. After preparing these implants, they need to be sterilized prior to packing. Sterilization at high temperatures and at higher gamma radiation results in chemical degradation. These O'Neill implants are reported to be sterilized at gamma radiation between a minimum of 25 kGy and no more than 40 kGy. Experiments by the present inventors show that the release of noroxymorphone is high when naltrexone is sterilized at a minimum radiation of 25 kGy, and this noroxymorphone degradation product is toxic in nature. Therefore, the content of noroxymorphone should be minimized so as to eliminate the side effects of these implants.

There are further naltrexone implants currently registered/unregistered/under development/registration by few companies in China, Europe and USA, as depicted below in table 1.

TABLE 1

| Formulation | Registration Status | Company | Brand | Strength | Dosing Regime |
|---|---|---|---|---|---|
| Tablet | Registered (in India & RoW) | Several companies | Several Brands | 50 mg | 50 mg once daily for up to 12 weeks |
| Injectable Depot | Registered (in US) | Alkermes (US) | Vivitrol | 380 mg | Monthly Depot injection |
| Naltrexone Implant | Registered (in Russia) | Fidelity Capital (Russia) | Prodetoxone | 1000 mg | 3-month implant |
|  | Under registration | Rusan Pharma | Addtrex Implant | 765 mg | 3-month implant |

TABLE 1-continued

| Formulation | Registration Status | Company | Brand | Strength | Dosing Regime |
|---|---|---|---|---|---|
| | (India, UK & Europe) | (India) | | | |
| | Unregistered | Go Medical Industries (Australia) | O'Neill Implants | 1500 mg | 2-month implant |
| | Unregistered | Civil Life (China) | Chinese Implants | 1850 mg | |

In summary, prior art naltrexone implantable tablets suffer from several disadvantages which limit their utility. Magnesium stearate or metal salts in general cause irritation and inflammation at the site of the implantation when combined with naltrexone in implantable tablets. Reduction of such irritation and inflammation has been attempted by combining the naltrexone compositions containing magnesium salts with triamcinolone, but such corticosteroids often cause side effects which limit their use. Further, the problem of the Toxic degradation product noroxymorphone remains unaddressed.

Accordingly, disclosed herein is a composition and process for naltrexone implantable tablets, which resolves the issues and concerns and side effects associated with magnesium salts, triamcinolone and noroxymorphone generated by sterilization with higher gamma radiation.

DESCRIPTION OF DRAWINGS

FIG. 1 shows % drug released per day over a period of 2 months.

SUMMARY OF THE INVENTION

Accordingly, provided herein are naltrexone implantable tablet compositions which are devoid of magnesium salts and triamcinolone so as to reduce additional metabolic load and toxicity on the liver, as well as other side effects.

In certain embodiments, provided herein is a naltrexone implantable tablet composition which comprises naltrexone embedded in biodegradable polymers comprising one or more DL-lactides and/or DL glycolides, or copolymers thereof, along with Eudragit (NE30D, NE40D, RS100, RL100 and other forms of Eudragit that allows sustained release of the active) and at least one lubricant to provide a controlled amount of naltrexone over a period of about 3 to about 6 months or more.

Lubricants are useful for the production of implants, added in small quantities to tablet formulations to improve certain processing characteristics such as for decreasing the friction, to prevent sticking to tablet punch and to improve the flow properties of the product by reducing interparticulate friction. Magnesium stearate is routinely employed lubricant in the tablet formulations. In a preferred embodiment, magnesium stearate as lubricant is not included in the present implantable tablet formulation, so as to avoid tissue irritation and inflammation at the site of the implantation. In certain embodiments, the lubricant is selected from stearic acid or glyceryl monostearate or combination thereof.

In certain embodiments, naltrexone implantable tablet compositions disclosed herein comprise 500 mg to 2 gms of naltrexone, e.g., 765 mg or 903 mg of naltrexone which were found to be suitable to release naltrexone above the therapeutic level of about 1 ng/ml in blood for about 3 to about 6 months or more.

DETAILED DESCRIPTION OF THE INVENTION

Embodiments of the invention will now be described in detail, including certain preferred and optional embodiments, so that various aspects thereof may be more fully understood and appreciated.

Disclosed herein are naltrexone implantable tablet compositions which are devoid of metal salts including magnesium salts such as magnesium stearate and corticosteroids such as triamcinolone, prednisolone, hydrocortisone, and salts thereof.

Naltrexone implantable tablets formulated without metal salts such as magnesium stearate or corticosteroids such as triamcinolone acetonide, and not sterilized by irradiation above 25 kGy, avoid side effects such as significant loss of body weight and lethargy, reduce potential carcinogenicity, reduce overall drug burden and minimize drug-drug interactions, paving the way for achieving ease of regulatory compliance, since pharmacovigilance requires reporting of adverse drug reactions. In certain embodiments, the implantable tablet composition comprises naltrexone in an amount of 500 to 2000 mg.

In certain embodiments, the naltrexone implantable tablet composition comprises naltrexone embedded in one or more biodegradable polymers or polyesters. In certain embodiments, the biodegradable polymer/polyester comprises one or more DL-lactides and/or DL glycolides, or copolymers thereof. In certain embodiments, the biodegradable polymer/polyester is a DL-lactide/glycolide copolymer and can be used in an amount of 20 mg to 100 mg.

In certain embodiments, the naltrexone implantable tablet composition comprises a polymethacrylate-based copolymer. In certain embodiments, the copolymer is based on methacrylic acid or methacrylic/acrylic esters or their derivatives. In certain embodiments, the copolymer is Eudragit®. Eudragit copolymer may be selected from Eudragit® NE, RS, RL and NM grades that are neutral ester dispersions which do not require additional plasticizers. One preferred Eudragit copolymer is Eudragit® NE 30 D, Eudragit® NE 40 D, Eudragit® NM 30 D Eudragit® RS100 and Eudragit® RL100. One preferable Eudragit copolymer is Eudragit® NE 30 D which is the aqueous dispersion of a neutral copolymer based on ethyl acrylate and methyl methacrylate and can be used in an amount of 50 mg to 150 mg.

In certain embodiments, the naltrexone implantable tablet composition comprises a lubricant or is made with a lubricant. In certain embodiments, the lubricant is selected from stearic acid or glyceryl monostearate or the combination thereof for the production of the implant. In certain embodiments, Stearic acid may be used in an amount of 1 mg-30 mg and glyceryl monostearate may be used in an amount of 5 mg to 50 mg.

Also provided herein are methods of sterilization of implantable tablet compositions.

In certain embodiments, the naltrexone implantable tablet composition contains from about 500 to about 2000 mg naltrexone or a salt thereof. In certain embodiments, the implant contains about 765 mg naltrexone. In certain embodiments, the implant contains about 903 mg of naltrexone. In certain embodiments, the implant contains an amount of naltrexone suitable to release naltrexone above the therapeutic level of 1 ng/ml in blood for about 3 months or more.

In certain embodiments, the naltrexone implantable tablet composition comprises from one to five tablets. In certain embodiments, the naltrexone implantable tablet composition comprises one or two tablets. In certain embodiments, the naltrexone implantable tablet composition comprises a single tablet. In certain embodiments, the naltrexone implantable tablet composition comprises two tablets. In certain embodiments, the naltrexone implantable tablet composition comprises one or two tablets comprising a total of about 765 mg naltrexone or about 903 mg naltrexone.

In one preferred embodiment, the invention provides a naltrexone implantable tablet composition comprising about 765 mg in the form of a single tablet. In another preferred embodiment, the invention provides a naltrexone comprising about 765 mg implantable tablet composition in the form of two tablet system.

In the two tablet system of 765 mg of naltrexone implant, each tablet weighs about 485 mg and contains about 382.5 mg of naltrexone with the total strength being about 765 mg naltrexone and total weight of the implant being about 970 mg. The tablets of the two tablet implantable system comprise similar size and shape. However, the size of the tablet may vary based on the quantity of the naltrexone base and excipients thereof used in the preparation of the tablet.

For example, the dimensions of the single tablet comprising about 765 mg naltrexone with the total weight being about 970 mg, will be about 10.9 mm to about 11.2 mm diameter and about 11.4 mm length. The dimensions of the tablets of the two tablet implant system, each tablet comprising about 382.5 mg of naltrexone with the total weight of each tablet being 485 mg, will be about 8.4 mm to about 8.5 mm diameter and about 9.0 mm length.

As another example, the dimensions of the tablets of the two tablet implant system each tablet comprising 451.5 mg of naltrexone will have dimensions of about 8.4 mm to about 8.5 mm diameter and about 10.4 mm of length.

The main difference between one tablet and two tablet implant systems (and indeed other multi-tablet systems) is the shape and size of the tablet(s) in the implant and ease of implantation. For example, in order to meet continuous drug availability and better patient compliance & comfort, the size of the one tablet may be reduced by splitting the total amount of naltrexone into 2 tablets, each having the same strength, with the total naltrexone base being, e.g., 903 mg. As the dose of naltrexone increases, the size of a tablet comprising it also increases, and a one tablet implant system may give a bulging sensation when introduced into the body (e.g., in the lower abdominal wall). Even when placed under local anesthetic, a large tablet can cause discomfort to the patient and therefore, in certain embodiments, the two tablet implantable system is preferable over one tablet implant.

Biodegradable DL-lactides/glycolides are used for manufacture of naltrexone implant to control the release rate over a period of time. In certain embodiments, the period of time is at least three months. In certain embodiments, the period of time is at least about three months. In certain embodiments, the period of time is about three to about six months. In certain embodiments, the period of time is at least three months. In certain embodiments, the period of time is about 6 months or more. These polymers are available in different grades having varying lactide:glycolide compositions, such as 50:50, 65:35, 75:25, 85:15, 5:95, 15:85 and 25:75. In certain embodiments, 50/50 DL-lactide/glycolide co-polymer is preferred. Additionally, in certain embodiments, Eudragit® NE 30 D polymer is used in the production of the implant. Other Eudragit copolymers such as Eudragit® NE 30 D, Eudragit® NE 40 D, Eudragit® NM 30 D Eudragit® RS100 and Eudragit®RL100 may also be used to achieve the similar effect.

After making the implants, these implants were put into polypropylene syringes and packed in a heat sealable sterilizable pouch, which is subjected to EtO (Ethylene Oxide) sterilization. As EtO cannot penetrate metal/polymeric film pouches, aluminum pouches were not used as the final packaging material. Three time points, viz 4.5, 6, and 8 hours, were used for sterilization at a standard dose of EtO. Results were satisfactory with time point 8 hours. However, concern remained that the risk of residual EtO and ethylene chlorohydrin could cause lethal effects on the user or patient.

Therefore, the packed implants were subjected to gamma irradiation, which is more preferable than EtO sterilization. Sterilization by gamma irradiation from 8 to 25 kGy was attempted. No significant/appreciable change in the color, content and dissolution profile of the Naltrexone implantable tablets were observed at the lower intensity of gamma irradiation. Further, there was also no appreciable change in the impurity profile after irradiation, other than an increase in the content of noroxymorphone.

Accordingly, provided herein is a method of sterilization which method comprises subjecting the Naltrexone implants to gamma irradiation at intensity of 8-12 kGy so as to reduce the noroxymorphone degradation and yet maintaining the sterility of the product.

In yet another embodiment, the invention provides method for minimizing Noroxymorphone content in Naltrexone implantable tablet composition which method comprises subjecting the implantable composition to gamma irradiation at intensity of 8-12 kGy.

It was observed that initially the colour of the implants is white to off-white. On irradiation the colour changes through buff to yellowish to grayish green. This colour change depends on the intensity of the irradiation. It is observed to be yellowish at 8-12 kGy intensity and the colour deepens or changes to grayish green when the intensity is 25 kGy.

Types of syringes that can be used for implantation include those made of polypropylene (PP), polycarbonate (PC) and cyclic olefin copolymer (COC). There was no effect on the product with these syringes. PP syringes were more body compliant hence can be used.

An effective dose of Naltrexone is believed to be about 1 ng/ml in blood plasma. In the open label trial of naltrexone implants, the achieved naltrexone blood levels ranged from 5.2 ng/ml (1 month) to 0.9 ng/ml (6 months) and for 6 beta naltrexol the major active metabolite of naltrexone ranged from 9.1 ng/ml (1 month) to 3.5 ng/ml (6 months).

The naltrexone implants of the present invention successfully control the opiate dependency associated with the drugs such as heroin, morphine, codeine, oxycodone and methadone, in addition to alcohol dependence while maintaining the minimum therapeutic levels in the blood.

Thus, in yet another embodiment, provided herein is a method for reducing the alcohol and opiate dependency associated with drugs such as heroin, morphine, codeine, oxycodone and methadone in a subject, which method comprises implanting the naltrexone implantable tablet comprising naltrexone in an amount of 500 to 2000 mg, embedded in biodegradable polymers/polyesters along with Eudragit and a lubricant to provide a controlled amount of the active over a period of 3 months or more wherein, the composition is devoid of Magnesium salts and corticosteroids such as triamcinolone, prednisolone, hydrocortisone, and salts thereof.

While the preferred embodiment relates to naltrexone, however, other opioid receptor antagonists such as naloxone or nalmefene can also be used in the implantable formulations as discussed above. Accordingly, in a further embodiment, provided herein is an implantable tablet composition comprising an opioid antagonist, or a salt thereof, in an amount of 500 to 2000 mg, embedded in biodegradable polymers/polyesters along with Eudragit and a lubricant to provide a controlled amount of the active at least over a period of 3 months or more, wherein, the composition is devoid of Magnesium salts and corticosteroids. The opioid receptor antagonists according to this embodiment are selected from naltrexone, naloxone or nalmefene.

In certain optional embodiments, the implants may also contain other active agents such as anti-inflammatory agents, anti-histamine such as a corticosteroid which include but are not limited to Triamcinolone, dexamethasone, betamethasone, or anti-biotic agents such as cephalosporin embedded in the polymeric matrix along with naltrexone.

In a further embodiment, provided herein is a method for controlling the weight loss and lethargy in a subject undergoing a treatment for opiate and alcohol dependency while maintaining minimum therapeutic levels in the blood which method comprises implanting the naltrexone implantable tablet comprising naltrexone in an amount of 500 to 2000 mg, embedded in biodegradable polymers/polyesters along with Eudragit and a lubricant to provide a controlled amount of the active at least over a period of 3 months or more, wherein, the composition is devoid of Magnesium salts and corticosteroids.

The following terms have the meanings given below.

A "naltrexone implantable tablet composition" also referred to as "naltrexone implant." is a formulation of naltrexone suitable for implantation into a subject such that it releases naltrexone at a consistent and controlled rate over a long period of time, typically at least three months. A naltrexone implantable tablet composition may comprise one, two, or more tablets (also referred to as "naltrexone implantable tablets") implanted into the subject at any given time, in order to reach the desired level of naltrexone in the subject. When the naltrexone implantable tablet composition comprises, for example, two tablets, it is sometimes referred to herein as a "two tablet(s) implantable systems."

"Naltrexone" refers to a compound of the following structure:

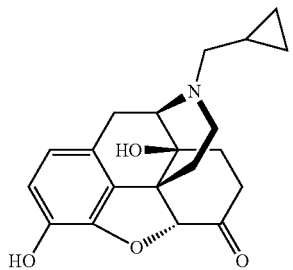

or a pharmaceutically acceptable salt, hydrate, or solvate thereof. The CAS registry number for naltrexone is 16590-41-3. Other names for naltrexone include: 17-(cyclopropylmethyl)-4,5α-epoxy-3,14-dihydroxymorphinan-6-one; (5α)-17-(cyclopropylmethyl)-3,14-dihydroxy-4,5-epoxy-morphinan-6-one; and (1S,5R,13R,17S)-4-(cyclopropylmethyl)-10,17-dihydroxy-12-oxa-4-azapentacyclo[9.6.1.01,13.05,17.07,18]octadeca-7(18),8,10-trien-14-one. Naltrexone hydrochloride (CAS Reg. No. 16676-29-2) has been marketed under the trade names Antaxone®, Depade®, Nalorex®, Revia®, Trexan®, Vivitrex®, and Vivitrol®.

A "naltrexone" refers to the amount of naltrexone to be delivered, absent the molecular weight of any salt counterion, associated solvate, etc.

The term "opioid overdose," as used herein, refers to an acute medical condition induced by excessive use of one or more opioids. Symptoms of opioid overdose include including respiratory depression (including postoperative opioid respiratory depression, acute lung injury, and aspiration pneumonia), central nervous system depression (which may include sedation, altered level consciousness, miotic (constricted) pupils), and cardiovascular depression (which may include hypoxemia and hypotension). Visible signs of opioid overdose or suspected opioid overdose include: unresponsiveness and/or loss of consciousness (won't respond to stimuli such as shouting, shaking, or rubbing knuckles on sternum); slow, erratic, or stopped breathing; slow, erratic, or stopped pulse; deep snoring or choking/gurgling sounds; blue or purple fingernails or lips; pale and/or clammy face; slack or limp muscle tone; contracted pupils; and vomiting. Because opioid overdose may be difficult to diagnose and/or quantify, particularly by a lay person, as used herein, treatment of opioid overdose is meant to include treatment of suspected opioid overdose in opioid-intoxicated patients. Opioids that may induce overdose include, codeine, morphine, methadone, fentanyl, oxycodone HCl, hydrocodone bitartrate, hydromorphone, oxymorphone, meperidine, propoxyphene, opium, heroin, tramadol, tapentadol, and certain narcotic-antagonist analgesics, such as, nalbuphine, pentazocine and butorphanol. In some embodiments, the opioid agonist is in a tamper-proof formulation. In some embodiments, the opioid agonist is in a tamper-resistant formulation. In some embodiments, the opioid agonist is selected from Acurox® Oxycodone DETERx®, Egalet hydrocodone, Egalet morphine, Egalet oxycodone, Exalgo®, Opana®, and Remoxy®.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "devoid of" as used herein means preferably less than 2.5%; more preferably less than 2%; still more preferably less than 1.5% and most preferably less than 1%. The term "biodegradable polymer" refers to a polymer or polymers which degrade in vivo, and wherein erosion of the polymer or polymers over time occurs concurrent with or subsequent to release of the therapeutic agent. A biodegradable polymer may be a homopolymer, a copolymer, or a polymer comprising more than two different polymeric units.

The following examples, which include preferred embodiments, will serve to illustrate the practice of this invention, it being understood that the particulars shown are by way of example and for purpose of illustrative discussion of preferred embodiments of the invention.

Example 1

Composition of One Tablet Implant System (Total Weight: 970 mg/Tab):
Naltrexone—765 mg
Stearic acid—2 mg
glyceryl monostearate—40 mg
DL-Lactide/Glycolide Co-Polymer—35 mg
Eudragit NE30D-120 mg
Manufacturing process: The implantable tablet of Naltrexone is prepared as per the method disclosed under example 2.

Example 2

Two Tablet Implant System, Weight: 485 mg/Tab) and Each Tablet Contains:
Naltrexone—382.50 mg
Stearic acid—1 mg
glyceryl monostearate—20.10 mg
DL-Lactide/Glycolide Co-Polymer—17.5 mg
Eudragit NE30D-60 mg
Manufacturing Process of the Implantable Tablet:

| Stage | Item Name | mg/tab |
| --- | --- | --- |
| Dry Mix | | |
| A | Naltrexone IH | 382.50 |
| A | Stearic acid | 1.00 |
| | Glyceryl monostearate | 20.10 |
| Mixture Preparation - I | | |
| B | 50/50 DL-Lactide/Glycolide Co-Polymer I.H. | 17.50 |
| B | Dichloromethane BP | 0.24 ml |
| B | Isopropyl Alcohol BP/Ph.Eur | 0.06 ml |
| Mixture Preparation - II | | |
| C | Eudragil NE 30 D IH | 60.00 |
| | TOTAL | 485.00 |

Dry Mix Preparation:
a) mixing Naltrexone and Stearic acid & Glyceryl monostearate in a planetary mixer for 5 minutes followed by unloading the blend after mixing in a polybag;

Mixture Preparation I:
b) mixing MDC and IPA in the ratio of 80:20 in a planetary mixer, followed by addition of 50/50 DL-Lactide/Glycolide Co-Polymer under stirring till complete dissolution;
c) adding the above dry mix of step a) into planetary mixer containing polymer solution and mixed further till granules are obtained and
d) discharging the granules into tray and subjected to aerial drying for a day.

Mixture Preparation II:
e) loading the mixture I granules in planetary mixer; adding Eudragit NE 30 D to it followed by mixing till granules are obtained taking care that no lump formation takes place;
f) discharging the granules into tray subjected to aerial drying for a day.
g) sizing the above granules by sifting through #20 and milling the oversized granules through 2.0 mm screen followed by transferring the sized granules into Cage blender and Blended for 5 minutes;
h) discharging the granules into clean labelled bins followed by recording the weight of sized granules and
i) compressing the above blend on a 16 station compression machine using 8.40 mm round deep concave punches.

Compression Details:
a) Punch Tools—Round shaped deep concave punches.
b) Average weight: 572.5 mg
c) Diameter: 8.3-8.7 mm
e) Hardness: 120 N to 220 N
f) Unload compressed tablets into clean bins lined with double polybag.
g) After QC release, send the tablets for packing.

Example 3

Sterilization Method:

As the implant is meant to be inserted under the human skin, its sterility plays an important role in the development of the dosage form and selection of a suitable sterilization method in order to get a sterile drug product. Sterilization was carried out by ethylene oxide sterilization (EtO) and Gamma sterilization.

Naltrexone tablets for implantation were kept into PP syringes and packed in a heat seal sterilizable pouch for EtO sterilization. As EtO cannot penetrate metal/polymeric film pouches, aluminium pouches were not used as the final packaging material. Three time points, 4.5, 6, and 8 hours, were used for sterilization at a standard dose of EtO, results were satisfactory with time point 8 hours. However, residual EtO, and its degradation product ethylene chlorohydrin (an organochlorine compound), may cause lethal effects. Therefore, for user safety concerns, gamma irradiation, which decomposes organochlorine compounds was carried out.

Gamma irradiation was carried out at various intensities/doses: 4 kGy, 8 kGy, 12 kGy, 16 kGy, 20 kGy, and 25 kGy. All the samples which were kept on and above 8 kGy passed the 14 day sterility test, while those at 4 kGy and 6 kGy failed to meet the test at the 8-10 days of sterility testing.

The sterilization by gamma irradiation from 8 to 25 kGy indicates no significant change in the content and dissolution profile. There was also no appreciable change in the impurity profile after irradiation, other than an increase in the content of Noroxymorphone, which is a degradation product of Naltrexone.

When the product was irradiated at 25 kGy, the initial noroxymorphone content was 0.5%. After accelerated studies (at 40° C. and RH of 75%) at 3 and 6 months it was found to be 1.54% and 1.6% respectively.

However, when the product was irradiated at 8 kGy, the initial noroxymorphone content was 0.45%. After accelerated studies (at 40° C. and RH of 75%) at 3 and 6 months it was found to be 0.64% and 0.68% respectively, and less than half of the noroxymorphone content obtained when sterilization is conducted at 25 kGy.

Thus irradiation of the product between 8 and 10 kGy, the initial noroxymorphone content was 0.4% on release and remains below 1% (between 0.4% and 0.9%) till the end of the shelf life of 2 years.

Also, the in-vitro dissolution profile too was substantially similar when irradiated at 8 kGy or 10 kGy for 1 tablet 765 mg implant and 2 tablet 765 mg implant.

Example 4

Drug Release:

An effective dose of Naltrexone is believed to be 1 ng/ml in blood plasma. In the open label trial of naltrexone implants, the achieved naltrexone blood levels ranged from 5.2 ng/ml (1 month) to 0.9 ng/ml (6 months), and for 6 beta naltrexol the major metabolite of naltrexone ranged from 9.1 ng/ml (1 month) to 3.5 ng/ml (6 months).

However, the implantable tablet composition of the Naltrexone according to the present invention releases a dose of about 0.9 mg/day to 15 mg/day in vitro to give a targeted effective dose of about 1 ng/ml to 5.2 ng/ml per day in vivo over a period of 3 months or more.

Example 5

An exemplary embodiment of the tablet of Naltrexone implants along with its weight & dimensions are provided herein below. However, a person skilled in the art may suitably change the shape and size of the implant

| Implant | Diameter | Length | Weight/tablet |
|---|---|---|---|
| 765 mg 1 tab (765 mg naltrexone/tab) | 10.9-11.2 mm | About 11.4 mm | 970 mg |
| 765 mg 2 tab (382.5 mg naltrexone/tab) | 8.4-8.5 mm | About 9 mm | 485 mg |
| 903 mg 2 tab (451.5 mg naltrexone/tab) | 8.4-8.5 mm | About 10.4 mm | 572.5 mg |

Example 6

Drug Release of Naltrexone from Naltrexone Implant in Buffer Solution:

The drug release of naltrexone from naltrexone implant is demonstrated in buffer solution to imitate in-vivo condition using the method as follows: Two naltrexone-loaded polymer tablets were placed in 100 ml, 0.02 M phosphate buffer solution at pH 7.4 and maintained at 37° C. The samples were collected daily from the release medium and the entire release medium was replaced daily with fresh buffer for first month and there after weekly for next two months. The amount of naltrexone released in solution was quantified by an UV spectrophotometer at 281 nm.

Preparation of 0.02M Phosphate Buffer pH 7.4 (Release Medium):

2.7218 gm of potassium dihydrogen orthophosphate (KH2PO4) was dissolved in about 900 ml water. Adjusted the pH to 7.4 with 20% sodium hydroxide solution and the volume was made up to 1000 ml with water & mixed well.

Sample Preparation:

Two naltrexone tablets with a total content of 765 mg or 903 mg naltrexone were slowly transferred to a 100 ml volumetric flask and made up the volume to 100 ml with the Release medium. The flask was closed with stopper and kept undisturbed at 37° C. After 24 hours, sample was collected daily by filtration. The tablet was transferred back to a 100 ml volumetric flask & the entire 100 ml Release medium was replaced by a fresh buffer solution. This operation was continued for 90 days. 5 ml of the filtrate was diluted to 50 ml with the release medium.

Standard Preparation:

Weighed accurately about 50 mg of naltrexone base and transferred to 100 ml volumetric flask; added about 80 ml of the release medium and sonicated to dissolve naltrexone. The volume was made up to 100 ml with the release medium and mixed well. 5 ml of the resultant solution was diluted to 25 ml with the release medium and mixed well.

The absorbance of the sample preparation and the standard preparation was measured at 281 nm in 1 cm cell against the release medium as a blank on a suitable spectrophotometer.

Calculation:

Calculation:

$$\frac{\text{Sample absorbance} \times 100 \times 50 \times \text{wt. of } std \text{ in mg} \times 5 \times \% \text{ purity of } std \text{ as is}}{\text{Standard absorbance} \times 1 \times 2 \times 100 \times 50 \times 100} =$$

mg of Naltrexone released per day.

$$\% \text{ drug released per day} = \frac{\text{mg of Naltrexone released per day} \times 100}{765}$$

Percent drug released per day is shown in the below tables 1 to 3 and also in FIG. 1.

TABLE 1

| B. No. | Days | | | | | | | | | | | | | | |
|---|---|---|---|---|---|---|---|---|---|---|---|---|---|---|---|
| 6401401 Tablets | 1 mg | 2 mg | 3 mg | 4 mg | 5 mg | 6 mg | 7 mg | 8 mg | 9 mg | 10 mg | 11 mg | 12 mg | 13 mg | 14 mg | 15 mg |
| 1 | 14.5 | 10.6 | 8.8 | 8.6 | 5.3 | 5.3 | 5.3 | 6.3 | 5.9 | 1.0 | 5.1 | 4.5 | 4.5 | 4.5 | 11.9 |
| 2 | 14.5 | 9.7 | 9.4 | 8.3 | 5.3 | 5.3 | 5.3 | 5.6 | 5.9 | 0.7 | 5.5 | 4.4 | 4.4 | 4.4 | 11.9 |
| 3 | 16.5 | 10.0 | 8.5 | 8.6 | 5.2 | 5.2 | 5.2 | 5.9 | 5.6 | 1.0 | 5.1 | 4.3 | 4.3 | 4.3 | 11.3 |

TABLE 1-continued

| | | | | | | | | | | | | | | |
|---|---|---|---|---|---|---|---|---|---|---|---|---|---|---|
| 4 | 14.5 | 9.4 | 9.4 | 7.6 | 5.4 | 5.4 | 5.4 | 6.3 | 5.9 | 0.7 | 5.5 | 4.4 | 4.4 | 4.4 | 11.6 |
| 5 | 14.8 | 10.0 | 8.5 | 7.3 | 5.4 | 5.4 | 5.4 | 5.6 | 5.9 | 3.8 | 5.5 | 4.7 | 4.7 | 4.7 | 11.3 |
| 6 | 15.2 | 11.0 | 8.8 | 7.6 | 5.6 | 5.6 | 5.6 | 5.6 | 5.9 | 4.5 | 5.5 | 4.7 | 4.7 | 4.7 | 11.9 |
| Avg | 15.0 | 10.1 | 8.9 | 8.0 | 5.4 | 5.4 | 5.4 | 5.9 | 5.9 | 2.0 | 5.4 | 4.5 | 4.5 | 4.5 | 11.7 |

| B. No. | Days | | | | | | | | | | | | | | |
|---|---|---|---|---|---|---|---|---|---|---|---|---|---|---|---|
| 6401401 Tablets | 16 mg | 17 mg | 18 mg | 19 mg | 20 mg | 21 mg | 22 mg | 23 mg | 24 mg | 25 mg | 26 mg | 27 mg | 28 mg | 29 mg | 30 mg |
| 1 | 4.4 | 4.1 | 5.8 | 2.7 | 2.7 | 2.7 | 7.1 | 3.2 | 3.3 | 2.3 | 2.9 | 2.9 | 2.9 | 2.6 | 1.9 |
| 2 | 3.8 | 3.8 | 5.8 | 2.6 | 2.6 | 2.6 | 7.1 | 2.9 | 3.3 | 2.6 | 3.1 | 3.1 | 3.1 | 2.6 | 1.9 |
| 3 | 4.1 | 3.8 | 5.5 | 2.3 | 2.8 | 2.8 | 7.1 | 2.6 | 3.3 | 2.3 | 3.2 | 3.2 | 3.2 | 2.9 | 2.3 |
| 4 | 4.1 | 3.2 | 6.1 | 2.7 | 2.7 | 2.7 | 7.1 | 2.6 | 3.6 | 2.6 | 3.3 | 3.3 | 3.3 | 2.9 | 2.6 |
| 5 | 4.8 | 3.2 | 6.1 | 2.8 | 2.8 | 2.8 | 7.1 | 2.9 | 3.6 | 2.3 | 2.6 | 2.6 | 2.6 | 4.2 | 2.3 |
| 6 | 4.4 | 3.8 | 5.5 | 2.7 | 2.7 | 2.7 | 7.1 | 2.9 | 3.6 | 2.6 | 2.3 | 2.3 | 2.3 | 3.9 | 2.3 |
| Avg | 4.3 | 3.7 | 5.8 | 2.7 | 2.7 | 2.7 | 7.1 | 2.9 | 3.5 | 2.5 | 2.9 | 2.9 | 2.9 | 3.2 | 2.2 |

TABLE 2

| B. No. | Days | | | | | | | | | | | | | | |
|---|---|---|---|---|---|---|---|---|---|---|---|---|---|---|---|
| 6401401 Tablets | 31 mg | 32 mg | 33 mg | 34 mg | 35 mg | 36 mg | 37 mg | 38 mg | 39 mg | 40 mg | 41 mg | 42 mg | 43 mg | 44 mg | 45 mg |
| 1 | 1.9 | 1.9 | 1.9 | 1.9 | 1.9 | 1.9 | 1.9 | 1.6 | 1.6 | 1.6 | 1.6 | 1.6 | 1.6 | 1.6 | 1.5 |
| 2 | 1.9 | 1.9 | 1.9 | 1.9 | 1.9 | 1.9 | 1.9 | 1.7 | 1.7 | 1.7 | 1.7 | 1.7 | 1.7 | 1.7 | 1.5 |
| 3 | 1.8 | 1.8 | 1.8 | 1.8 | 1.8 | 1.8 | 1.8 | 1.7 | 1.7 | 1.7 | 1.7 | 1.7 | 1.7 | 1.7 | 1.6 |
| 4 | 1.9 | 1.9 | 1.9 | 1.9 | 1.9 | 1.9 | 1.9 | 1.5 | 1.5 | 1.5 | 1.5 | 1.5 | 1.5 | 1.5 | 1.6 |
| 5 | 2.0 | 2.0 | 2.0 | 2.0 | 2.0 | 2.0 | 2.0 | 1.5 | 1.5 | 1.5 | 1.5 | 1.5 | 1.5 | 1.5 | 1.5 |
| 6 | 1.9 | 1.9 | 1.9 | 1.9 | 1.9 | 1.9 | 1.9 | 1.7 | 1.7 | 1.7 | 1.7 | 1.7 | 1.7 | 1.7 | 1.6 |
| Avg | 1.9 | 1.9 | 1.9 | 1.9 | 1.9 | 1.9 | 1.9 | 1.6 | 1.6 | 1.6 | 1.6 | 1.6 | 1.6 | 1.6 | 1.6 |

| B. No. | Days | | | | | | | | | | | | | | |
|---|---|---|---|---|---|---|---|---|---|---|---|---|---|---|---|
| 6401401 Tablets | 46 mg | 47 mg | 48 mg | 49 mg | 50 mg | 51 mg | 52 mg | 53 mg | 54 mg | 55 mg | 56 mg | 57 mg | 58 mg | 59 mg | 60 mg |
| 1 | 1.5 | 1.5 | 1.5 | 1.5 | 1.5 | 1.5 | 1.1 | 1.1 | 1.1 | 1.1 | 1.1 | 1.1 | 1.1 | 0.9 | 0.9 |
| 2 | 1.5 | 1.5 | 1.5 | 1.5 | 1.5 | 1.5 | 1.1 | 1.1 | 1.1 | 1.1 | 1.1 | 1.1 | 1.1 | 0.9 | 0.9 |
| 3 | 1.6 | 1.6 | 1.6 | 1.6 | 1.6 | 1.6 | 1.0 | 1.0 | 1.0 | 1.0 | 1.0 | 1.0 | 1.0 | 0.9 | 0.9 |
| 4 | 1.6 | 1.6 | 1.6 | 1.6 | 1.6 | 1.6 | 1.0 | 1.0 | 1.0 | 1.0 | 1.0 | 1.0 | 1.0 | 0.8 | 0.8 |
| 5 | 1.5 | 1.5 | 1.5 | 1.5 | 1.5 | 1.5 | 1.1 | 1.1 | 1.1 | 1.1 | 1.1 | 1.1 | 1.1 | 1.0 | 1.0 |
| 6 | 1.6 | 1.6 | 1.6 | 1.6 | 1.6 | 1.6 | 1.1 | 1.1 | 1.1 | 1.1 | 1.1 | 1.1 | 1.1 | 1.0 | 1.0 |
| Avg | 1.6 | 1.6 | 1.6 | 1.6 | 1.6 | 1.6 | 1.1 | 1.1 | 1.1 | 1.1 | 1.1 | 1.1 | 1.1 | 0.9 | 0.9 |

TABLE 3

| B. No. | Days | | | | | | | | | | | |
|---|---|---|---|---|---|---|---|---|---|---|---|---|
| 6401401 Tablets | 61 mg | 62 mg | 63 mg | 64 mg | 65 mg | 66 mg | 67 mg | 68 mg | 69 mg | 70 mg | 71 mg | 72 mg |
| 1 | 0.9 | 0.9 | 0.9 | 0.9 | 0.9 | 0.9 | 0.9 | 0.9 | 0.9 | 0.9 | 0.9 | 0.9 |
| 2 | 0.9 | 0.9 | 0.9 | 0.9 | 0.9 | 0.9 | 0.9 | 0.9 | 0.9 | 0.9 | 0.9 | 0.9 |
| 3 | 0.9 | 0.9 | 0.9 | 0.9 | 0.9 | 0.8 | 0.8 | 0.8 | 0.8 | 0.8 | 0.8 | 0.8 |
| 4 | 0.8 | 0.8 | 0.8 | 0.8 | 0.8 | 0.9 | 0.9 | 0.9 | 0.9 | 0.9 | 0.9 | 0.9 |
| 5 | 1.0 | 1.0 | 1.0 | 1.0 | 1.0 | 0.8 | 0.8 | 0.8 | 0.8 | 0.8 | 0.8 | 0.8 |
| 6 | 1.0 | 1.0 | 1.0 | 1.0 | 1.0 | 0.8 | 0.8 | 0.8 | 0.8 | 0.8 | 0.8 | 0.8 |
| Avg | 0.9 | 0.9 | 0.9 | 0.9 | 0.9 | 0.9 | 0.9 | 0.9 | 0.9 | 0.9 | 0.9 | 0.9 |

Example 7

Development of Dissolution Medium to Check the Batch to Batch Consistency

Media provides sink conditions for maximum release of the drug from pharmaceutical system as well as aids in solubilization of drug for release; therefore, proper selection of media can be important. Media of different pH was used for selection of the correct media for dissolution of the naltrexone implantable tablets. The following five dissolution media were used from pH ranging from 1.2 to 7.4. The pH above 7.4 was not used, as the drug solubility is reduced at pH above 7.4.

Different Mediums Used:
 1. 0.1 M Hydrochloric acid, pH 1.2
 2. Phosphate buffer, pH 4.5
 3. Water, pH 6.2
 4. Phosphate buffer pH 7 0.4+1.0% Sodium lauryl sulphate (SLS)+0.02% Sodium Azide, pH 7.4
 5. Phosphate buffer pH 7.4+0.2% Tween 80+0.02% Sodium Azide, pH 7.4 Out of all the above media, the medium containing 0.1 M hydrochloric acid, pH 1.2 provides complete release of the Natrexone implant in 24 hrs and thus further considered for the evaluation of quality consistency (precision) of different batches of Naltrexone implants.

Accordingly Naltrexone Implant (3 months), of three different batches were tested for dissolution by employing the medium containing 0.1 M Hydrochloric acid, pH 1.2 and the results obtained were statistically evaluated for percentage coefficient of variation. The results of all the three batches were found statistically similar. Hence, the method was found to be precise for the quality check/consistency of different batches of Naltrexone implantable tablets. On the basis of above results, following method parameters were finalized for Batch to Batch consistency applied for batch release.

Apparatus: Paddle apparatus USP 2
Media: 0.1 M Hydrochloric acid
Volume: 1000 ml
Temperature of media: 37° C.
Replacement volume: 10 ml
RPM: 100
Time Intervals and Cumulative percentage release limits: to be recorded

| Time | Acceptance criteria |
|---|---|
| 1 | NMT 40% |
| 2 | 30-55% |
| 4 | 40-70% |
| 8 | 60-90% |
| 12 | NLT 75% |

Example 8

Clinical Trials:

In a larger (2 trials, one on 21 opioid patients, $2^{nd}$ on 29 alcohol patients) clinical trial conducted ion 50 patients having various alcohol and opiate dependence, after implantation of the Naltrexone tablets of the present invention from day 1 to day 90, it has been observed that there was no craving for alcohol and no opiate was detected in urine analysis. This observation confirms that the naltrexone implants of the present invention blocks the effects of opiate drugs thereby induces abstinence towards alcohol and opiate drugs in patients who are dependent on them. This study further confirms that the implants of the present invention release a controlled amount of naltrexone over a period of at least for 3 months, so as to maintain minimum therapeutic levels in the blood.

Comparison of implants using triamcinolone in the composition and without use of triamcinolone in the composition have resulted in the observation that implants containing triamcinolone lead to weight loss and lethargy while implants not containing triamcinolone have successfully achieved desirable opiate blockage without having side effects, as disclosed herein.

Example 9

Animal Toxicity Study of Naltrexone Implant:

This study was undertaken for a comparative safety assessment of Naltrexone implant containing 191.25 mg Naltrexone & 7.5 mg Triamcinolone acetonide; Triamcinolone acetonide alone (250 mg Tablet containing 7.5 mg Triamcinolone acetonide) and Naltrexone alone (250 mg Tablet containing 191.25 mg Naltrexone) after single subcutaneous impanation in male Sprague Dolly rats. 24 male Sprague Dolly rats were randomized into 4 groups. At the start of the treatment, the body weight variation of animals was within the range of ±20% of the mean body weight of each sex.

The groups were identified as follows.
Group 1: Control (250 mg Placebo containing equivalent quantity of polymer and balance inactive material)
Group 2: Naltrexone alone (250 mg Tablet containing 191.25 mg Naltrexone)
Group 3: Triamcinolone acetonide alone (250 mg Tablet containing 7.5 mg Triamcinolone acetonide)
Group 4: Naltrexone+Triamcinolone acetonide (250 mg Tablet containing 191.25 mg Naltrexone & 7.5 mg Triamcinolone acetonide).

At the end of 15 days study period, the study revealed body weight reductions in animals treated with Triamcinolone acetonide alone and the combination of Naltrexone and Triamcinolone acetonide and also reduction in the growth of the animals. Animals belonging to Triamcinolone acetonide alone and the combination of Naltrexone and Triamcinolone acetonide groups appeared lethargic also. In naltrexone alone treated animals a slight reduction in the body weight was observed when compared with a control placebo group. Further, external and internal examination of implantation sites did not reveal any differences with respect to inflammatory reactions between the different groups.

From the above study, it is apparent that the group 2, where the Natrexone alone implanted is safe and less toxic with reduced side effects such as extreme body weight reduction and lethargy when compared to the groups 3 &4 implanted with Naltrexone and Triamcinolone acetonide and Triamcinolone acetonide alone tablets respectively. Thus, the implantable tablet composition comprising naltrexone without using magnesium or metal salts and corticosteroids not only minimizes the inflammation at the site of implantation but also reduces extreme weight loss and lethargy.

INDUSTRIAL ADVANTAGES

The naltrexone implantable tablets as provided in the present invention has advantages over the implantable tablets disclosed in prior art such as, avoided adverse drug-drug interactions, side effects such as significant reduction in body weight and lethargy, inflammation and itching at the site of implantation, optimally sterilized product with reduced impurities, provides controlled amount of naltrexone release for 3-6 months, ease of insertion, comfort to the patient and convenience of implantation.

We claim:
1. A naltrexone implantable tablet composition comprising naltrexone in an amount of 500 to 2000 mg, wherein, the composition is devoid of magnesium salts and corticosteroids, to provide a controlled amount of the active over a period of 3 months or more;
   wherein the implantable tablet composition comprises a granulate of 20 to 100 mg of a biodegradable polyester and the naltrexone.
2. The naltrexone implantable tablet composition according to claim 1, wherein, the composition further comprises a lubricant; and wherein the granulate is obtained by wet granulation.
3. The naltrexone implantable tablet composition according to claim 2, wherein, the biodegradable polyester is selected from the group consisting of DL-lactides, glycolides, and mixtures thereof.
4. The naltrexone implantable tablet composition according to claim 3, wherein, the polymer is DL-lactide/glycolide copolymer, wherein a ratio of lactide to glycolide in the copolymer is between 85:15 and 5:95.
5. The naltrexone implantable tablet composition according to claim 1, further comprising a (meth)acrylic ester copolymer providing pH-independent swelling.
6. The naltrexone implantable tablet composition according to claim 2, wherein, the lubricant is selected from stearic acid, glyceryl monostearate or combination thereof.

7. The naltrexone implantable tablet composition according to claim 1, wherein, the strength of the Naltrexone is about 765 mg or about 903 mg.

8. The naltrexone implantable tablet composition according to claim 1, wherein, the tablet composition is provided as a one tablet or two tablet system.

9. The naltrexone implantable tablet composition according to claim 1, wherein, the composition releases a dose of about 0.9 mg/day to 15 mg/day in vitro to give a targeted effective dose of about 1 ng/ml to 5.2 ng/ml per day in vivo over a period of 3 months or more.

10. The naltrexone implantable tablet composition according to claim 1, comprising dimensions of about 2 mm to 12 mm diameter and 0.5 cm to 3 cm length.

11. The naltrexone implantable tablet composition according to claim 10, wherein, the tablet comprising 8.5 mm-11.2 mm diameter and about 9 mm-11.4 mm in length.

12. The naltrexone implantable tablet composition according to claim 1, wherein, the composition optionally comprises additional active agent selected from the group consisting of an anti-biotic agent, an anti-inflammatory agent, and an anti-histamine.

13. A method of sterilization of the naltrexone implantable tablet composition according to claim 1 so as to reduce the post-sterilization noroxymorphone in the composition which method comprises subjecting the naltrexone implantable tablet composition to gamma irradiation at intensity of 8-25 kGy so as to maintain the sterility of the product.

14. The method as recited in claim 13, wherein, the gamma irradiation at intensity of 8-12 kGy.

15. A method of controlling the weight loss and lethargy in a subject undergoing a treatment for opiate and alcohol dependency while maintaining the effective daily dose of naltrexone in the blood which method comprises implanting a naltrexone implantable tablet according to claim 1 in the subject.

* * * * *